US012364611B2

(12) United States Patent
Unal et al.

(10) Patent No.: US 12,364,611 B2
(45) Date of Patent: Jul. 22, 2025

(54) TEST PLATFORM SYSTEM

(71) Applicant: OZYEGIN UNIVERSITESI, Istanbul (TR)

(72) Inventors: Ramazan Unal, Istanbul (TR); Ege Gediksiz, Istanbul (TR)

(73) Assignee: OZYEGIN UNIVERSITESI, Istanbul (TR)

( * ) Notice: Subject to any disclaimer, the term of this patent is extended or adjusted under 35 U.S.C. 154(b) by 287 days.

(21) Appl. No.: 18/033,562

(22) PCT Filed: Dec. 30, 2021

(86) PCT No.: PCT/TR2021/051625
§ 371 (c)(1),
(2) Date: Apr. 25, 2023

(87) PCT Pub. No.: WO2022/146398
PCT Pub. Date: Jul. 7, 2022

(65) Prior Publication Data
US 2023/0390088 A1    Dec. 7, 2023

(30) Foreign Application Priority Data
Dec. 30, 2020 (TR) ............... 2020/22548

(51) Int. Cl.
*A61F 2/76* (2006.01)
*G01M 99/00* (2011.01)

(52) U.S. Cl.
CPC ........ *A61F 2/76* (2013.01); *A61F 2002/7695* (2013.01); *G01M 99/008* (2013.01)

(58) Field of Classification Search
CPC ............... A61F 2/76; A61F 2002/7615; A61F 2002/7695; G01M 99/00; G01M 99/005; G01M 99/008; A61B 5/112
See application file for complete search history.

(56) References Cited

U.S. PATENT DOCUMENTS

| | | | |
|---|---|---|---|
| 2008/0021570 A1* | 1/2008 | Bedard | A61F 2/76 434/247 |
| 2015/0335450 A1 | 11/2015 | Coggins | |
| 2017/0119551 A1* | 5/2017 | Huang | A61F 2/72 |

FOREIGN PATENT DOCUMENTS

| | | | | |
|---|---|---|---|---|
| CN | 108635087 A | 10/2018 | | |
| CN | 108852567 A | 11/2018 | | |
| CN | 212082853 U | * 12/2020 | ............ | G01M 99/00 |
| JP | 2013503026 A | * 1/2013 | ............... | A61F 2/64 |

OTHER PUBLICATIONS

Alexander Poliakov, et al., System Analysis and Synthesis of Mechatronic Testbench for Testing Modules and Control Systems of Transfemoral Prostheses, The 2015 Biomedical Engineering International Conference, 2015.

Hanz Richter, et al., Dynamic modeling, parameter estimation and control of a leg prosthesis test robot, Applied Mathematical Modelling, 2015, pp. 559-573, vol. 39.

* cited by examiner

*Primary Examiner* — Benjamin R Schmitt
(74) *Attorney, Agent, or Firm* — Bayramoglu Law Offices LLC

(57) ABSTRACT

A test platform system for testing lower limb assistive devices includes a lower limb device, a guide system by which the movement of a lower limb device is simulated during its transition between positions, a second motor that performs the movement of the lower limb device, and a moving belt.

20 Claims, 4 Drawing Sheets

TEST PLATFORM SYSTEM

CROSS REFERENCE TO THE RELATED APPLICATIONS

This application is the national stage entry of International Application No. PCT/TR2021/051625, filed on Dec. 30, 2021, which is based on and claims priority to Turkish Patent Application No. 2020/22548, filed Dec. 30, 2020, the entire contents of which are incorporated herein by reference.

TECHNICAL FIELD

The present invention relates to a test platform system developed to replicate human movements for testing lower limb assistive devices.

BACKGROUND

Amputee patients not only suffer great physiological pain and psychic trauma, but also have to bear the burden of society and family. Current medical science and technology are not yet able to regenerate the deformed limb. For this reason, the recovery of patients can only be achieved with an artificial limb, i.e., by attaching the artificial limb that can function as a healthy limb to the patient. In this way, it is possible for the patients to perform basic functions of movement in daily life. One of the said artificial limbs is robotic lower limb devices. To test the performance of these lower limb devices, a functional simulation of the artificial limb system needs to be performed and tested, and evaluated accordingly.

Robotic lower limb assistive devices are highly important tools. Robotic lower limb assistive devices are used in rehabilitation of patients who have problems with their lower limbs, or enhancing the capability of human such as lifting or carrying high loads. Besides, testing and evaluation of these devices accurately has vital importance. Robotic testing has many advantageous aspects such as being able to perform long term operations and mimic dangerous conditions such as near-fall etc. Also, collecting data from test device is easier than collecting from human.

In the prior art, there is limited information about the test platforms that are used to test robotic lower limb assistive devices.

Alexander P., et al., 2015 describes a test platform that can solve a wide range of experimental tasks. Said test platform is primarily developed for testing artificial feet and represents a mechatronic device based on an electromechanically-driven Stewart platform. One of the connections of the test module is mounted on an upper fixed platform (rigid or hinged) and the second connection is supported or fixed on a movable platform. The mobile platform can perform many controlled movements, thus simulating the operation of the prosthetic module or control system tested.

Hanz R., et al., 2014 describes the development, modeling, parameter estimation and control of a robot capable of reproducing two degree-of-freedom hip motion in the sagittal plane. Hip vertical displacement and thigh angle motion profiles are applied to a transfemoral prosthesis attached to the robot. A treadmill is used as walking surface. Aside from tracking hip motion trajectories, the control system can be used to regulate the contact force between the treadmill and the prosthesis.

As for the devices in the state of the art, it is apparent that the mass is carried as a whole, i.e., the hip motions are not separated and therefore large motors are needed. In the prior art, there is still a need for a test platform system that can provide various motor movements while standing, walking, crouching, standing up, and overcoming obstacles, in order to examine the working ability of the controlled robotic lower limb devices that can perform hip motions separated from each other.

SUMMARY

An object of the invention is to provide a test platform that allows evaluation of the quality of a given product compared to its biological counterparts and, if necessary, to make changes in the design to provide the best possible quality of life for persons with disabilities while walking on the prosthesis.

Another object of the invention is to achieve a test platform that can simulate the complex conditions of human gait, incorporating the kinematics and dynamics of all elements of a healthy limb.

Another object of the invention is to achieve a test platform for moving the lower limb device, which prevents the lower limb device from generating more torque and enables the lower limb device to perform its natural movements.

Another object of the invention is to achieve a test platform system that can provide various motor movements while standing, walking, crouching, standing up and overcoming obstacles, in order to examine the working ability of the controlled robotic lower limb devices.

Another object of the invention is to achieve a test platform device that eliminates the risk of misinterpretation of the torque value in the testing of the lower limb devices used.

Still another object of the invention is to ensure that the lower limb device carries the load of the center of mass without being fixed to the test platform.

The invention relates to a test platform system for testing lower limb assistive devices in order to achieve the above purposes, including a lower limb device, a guide system by which the movement of a lower limb device is simulated during its transition between positions, a second motor that performs the movement of the lower limb device, and a moving belt. Said guide system includes a vertical rail element, a center of mass plate positioned on a rail element and movable upwards and downwards on the rail element, a vertical ball screw connected to a vertical rail element by means of at least one connection plate, wherein the ball screw is passed through a screw housing in the plate mounted on the rail element, a first motor positioned on the vertical ball screw and performing the center of mass plate (CoM) motion, at least one nut acting on the ball screw and converting the rotational movement of the first motor into a linear movement, wherein the center of mass plate is coupled with the nut via at least one ball bearing, at least one rod, and a nut plate that connects the nut to the at least one rod element.

The invention relates to a test platform system in which the ball screw is coupled with the second motor through a screw housing in the center of mass plate positioned on the rail element, in order to achieve the above purposes.

The invention relates to a test platform system in which the limb device under test is a transfemoral prosthesis, in order to achieve the above purposes.

The invention relates to a test platform system also including a hip unit that performs rotational movement of the transfemoral prosthesis, in order to achieve the above purposes.

The invention relates to a test platform system also including a connection link that connects the transfemoral prosthesis to the hip unit, in order to achieve the above purposes.

The invention relates to a test platform system in which the connection between the connection link and the hip unit is realized by means of its elements, in order to achieve the above purposes.

The invention relates to a test platform system in which the torque value of the hip unit reaches 120 Nm and the angular velocity thereof reaches 40 RPM so that the transfemoral prosthesis can simulate natural hip motion, in order to achieve the above purposes.

The invention relates to a test platform system in which the limb device under test is a robotic leg prosthesis, in order to achieve the above purposes.

The invention relates to a test platform system in which the limb device under test is an ankle prosthesis, in order to achieve the above purposes.

DESCRIPTION OF REFERENCES

Figure 1:
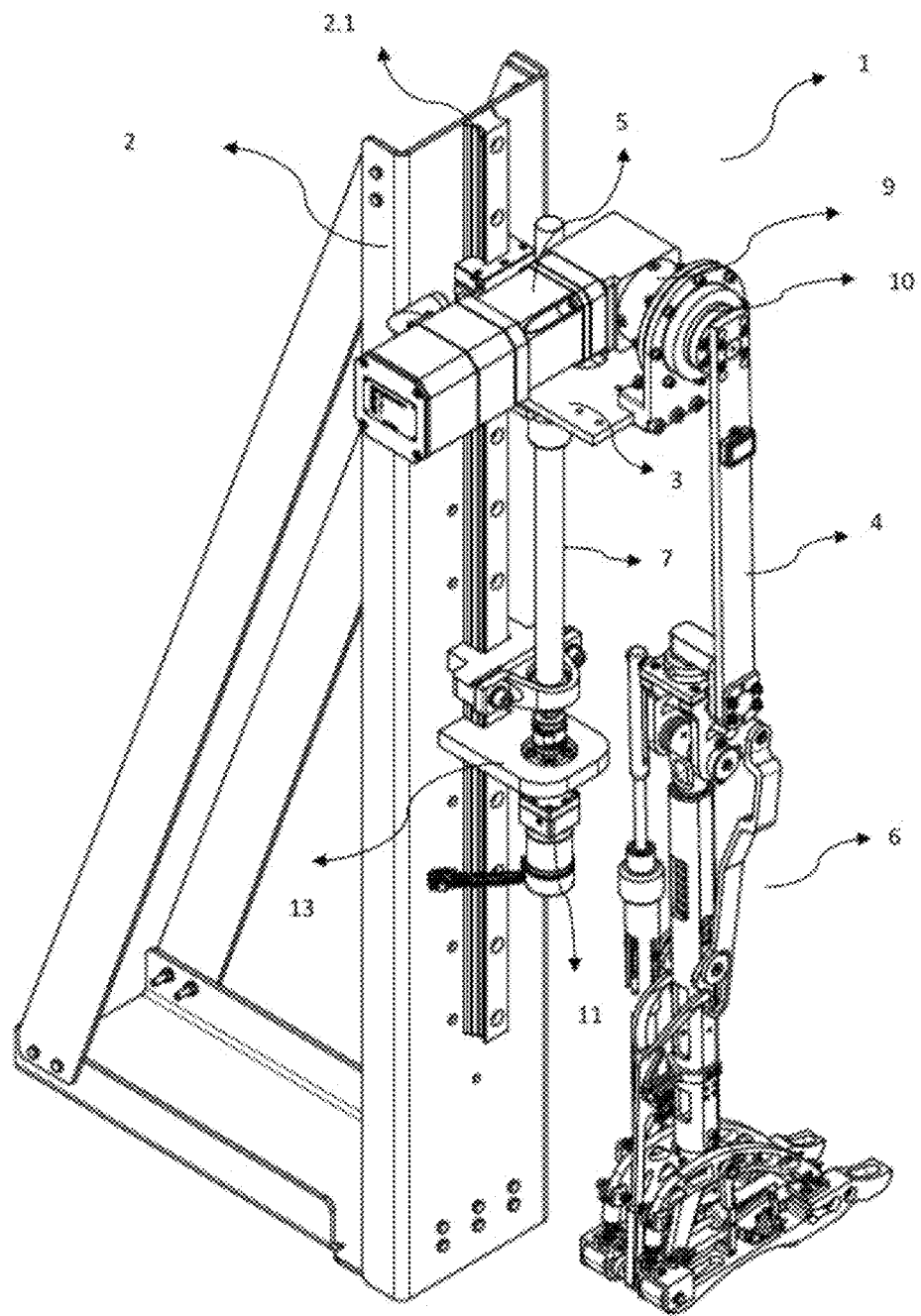
FIG. 1 is a front perspective view of a test platform system.
Figure 2:
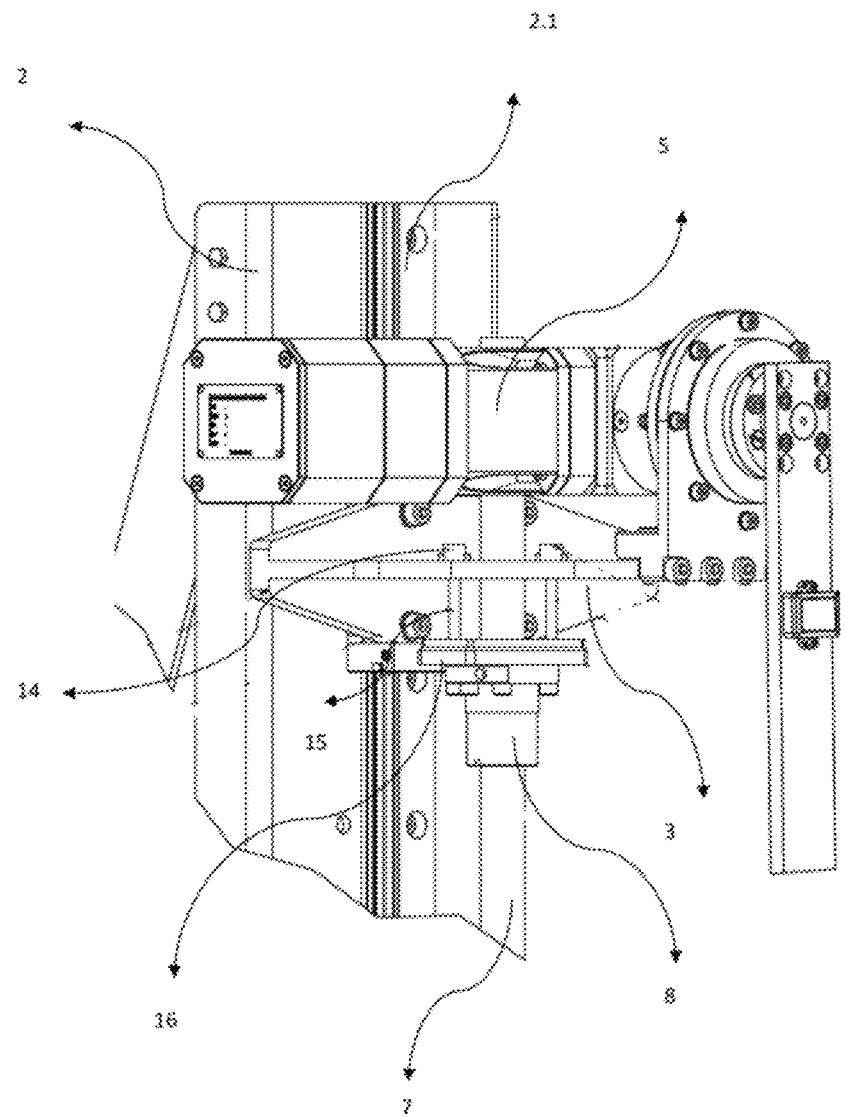
FIG. 2 is a front perspective view of a center of mass.
Figure 3:
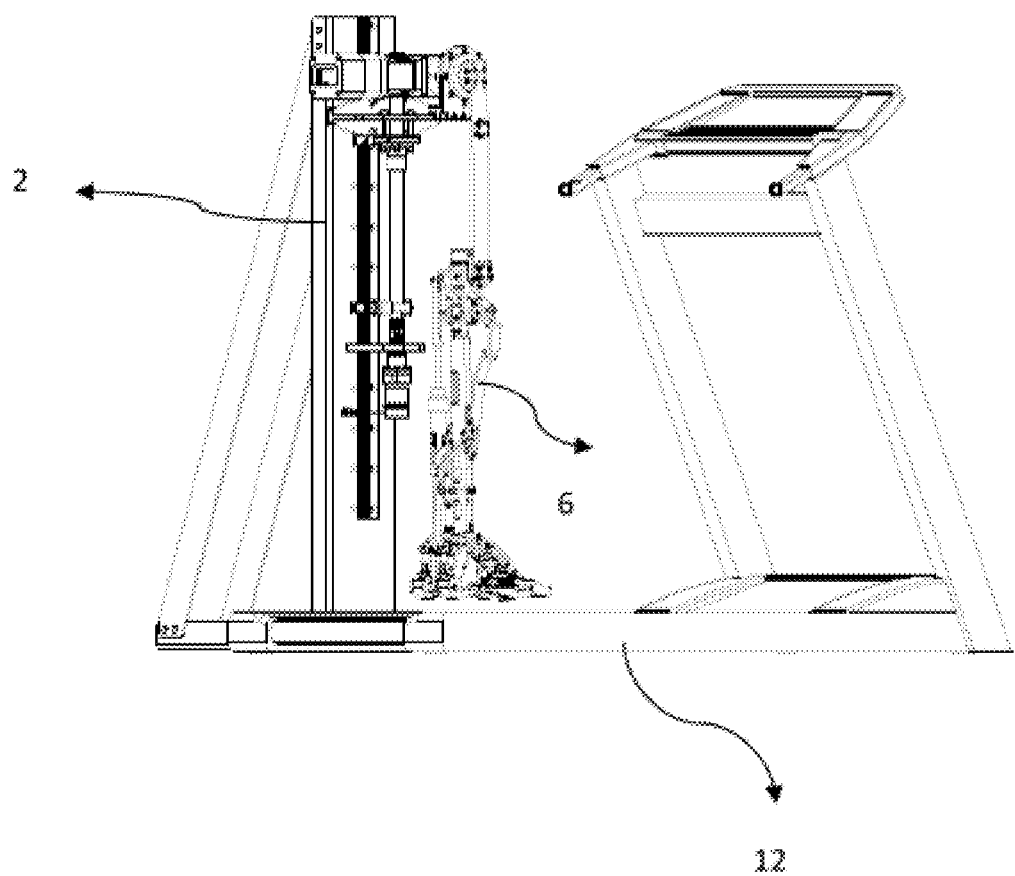
FIG. 3 is a view of the test platform system on the moving belt.
Figure 4:
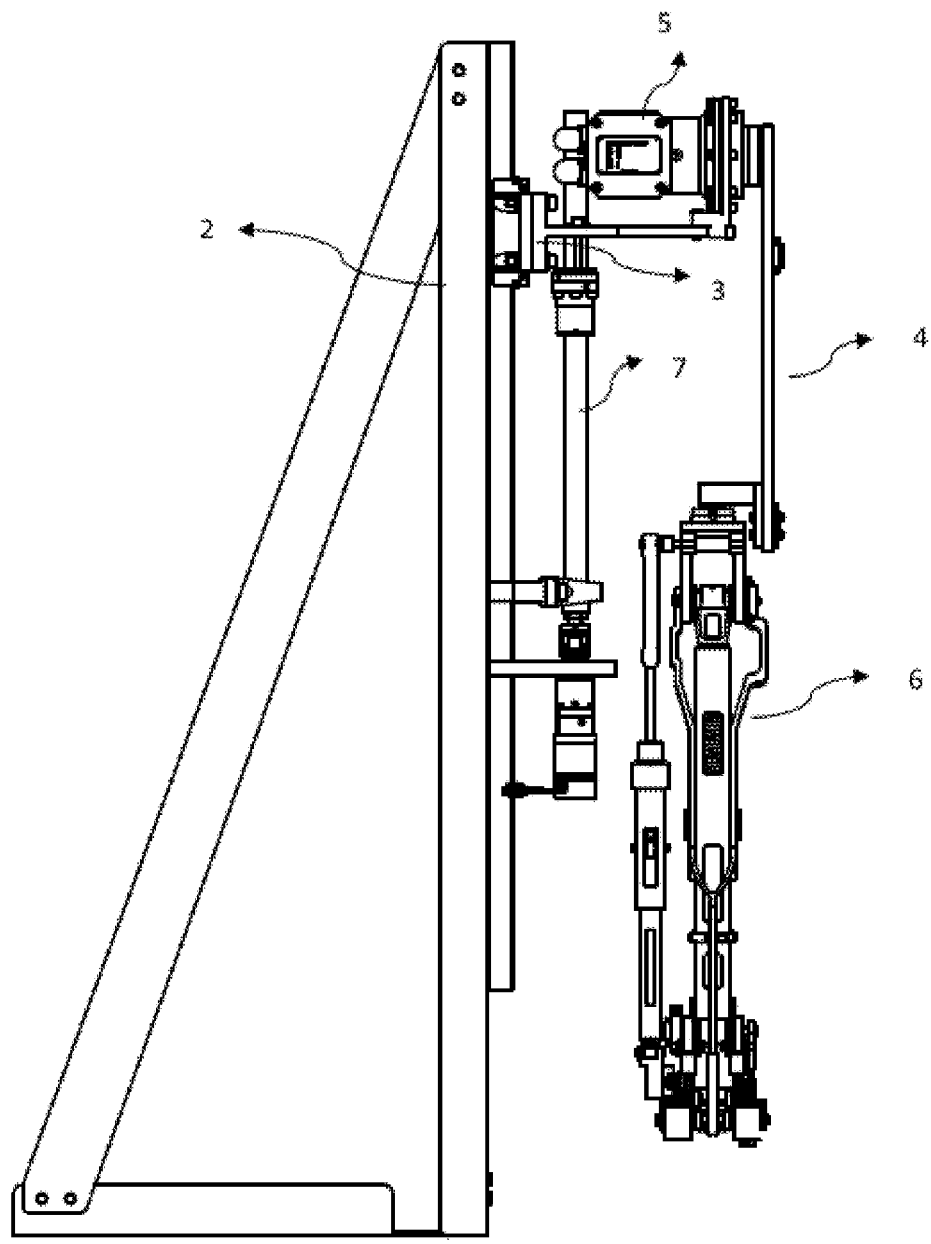
FIG. 4 is a rear perspective view of a test platform system.

1. Test platform system
2. Guide system
2.1 Rail element
3. Center of mass plate
4. Connection link
5. Second motor (Hip unit)
6. Transfemoral prosthesis
7. Ball screw
8. Nut
9. First connecting element
10. Second connecting element
11. First motor
12. Moving belt
13. Connection plate
14. Ball bearing
15. Rod
16. Nut plate

DETAILED DESCRIPTION OF THE EMBODIMENTS

The present invention relates to a test platform system (1) for testing lower limb assistive devices. With said test platform system (1), it is possible to test the ability of all kinds of lower limb assistive devices such as robotic leg prosthesis, ankle prosthesis and transfemoral prosthesis (6) to simulate the natural movements of a healthy limb.

The test platform system (1) of the invention includes a vertical guide system (2), a lower limb device, a second motor (5) that performs the movement of a lower limb device, a center of mass plate (3) that connects the second motor (5) and the vertical guide system (2), and a moving belt (12).

The guide system (2) of the test platform system (1) of the invention is a system in which the upward and downward movement of the center of mass plate (CoM) (3) is simulated during the transition of the lower limb device between positions. The guide system (2) includes a rail element (2.1), a center of mass plate (3) positioned on a rail element (2.1), a first motor (11), a ball screw (7) and a nut (8). The ball screw (7) converts the rotational movement of the first motor (11) into a linear movement and the nut (8) rotates and moves on said ball screw (7).

Initially, center of mass (CoM) motion was analyzed, and then data on the sufficient torque and power requirements of the lower limb device while walking at normal speed were evaluated in order to create conceptual designs for the test platform. Then, a prototype of the test platform system (1) was constructed using the first motor (11) that performs the center of mass (CoM) motion, and the second motor (5) enabling the movement of the lower limb device, with sufficient torque and power requirements.

With the present invention, the nut (8) is not secured to the guide system (2) of the center of mass (CoM) plate (3) in the test platform system (1). Therefore, it has a separate degree of freedom. With the present invention, the center of mass (CoM) load of the lower limb device can be carried during the stance phase. By not securing nut (8) of the ball screw (7) to the center of mass plate (3) (CoM), the lower limb device is prevented from generating more torque so as to rotate and move the inertia of the weight of the ball screw (7), the first motor (11), the first motor (11) coupling, and the nut (8), and it is ensured that the lower limb device performs its natural movements.

In the present invention, the connection of the first motor (11), which transmits the center of mass motion, with a rail element (2.1) located in the vertical guide system (2), is achieved by means of at least one connection plate (13). The first motor (11) and the nut (8) are positioned on the ball screw (7). Said ball screw (7) is passed through a screw housing in the center of mass plate (3) mounted on the rail element (2.1) and is connected to the second motor (5) by means of at least a first connecting element (9). The center of mass plate (3) is coupled with the nut (8) by means of at least one ball bearing (14), at least one rod (15), and a nut plate (16) which connects the nut (8) to the at least one rod (15). The torque transmitted by the second motor (5) is converted into a linear movement by way of the at least one rod (15). The ball bearing (14) supports the torque-loaded rod (15) and makes it move more smoothly. By converting the torque transmitted by the second motor (5) into the linear movement, the center of mass plate (3) (CoM) moves upwards and downwards on the rail element (2.1).

In the present invention, since the test platform system (1) has a fixed vertical guide system (2), a moving belt (12) is used as the walking surface. Since said moving belt (12) is a separate surface, compatibility with the vertical guide system (2) is checked. The moving belt (12) is a device on which the lower limb device simulates natural human movements and cooperates with the guide system (2).

Movements on the moving belt (12) can be controlled and speed can be adjusted. The speed of the motor in the moving belt (12) can be controlled.

In a basic embodiment of the invention, the lower limb device to be tested is a transfemoral prosthesis (6).

In the basic embodiment of the invention, the second motor (5) is a hip unit (5).

The test platform system (1) is a device in which the transfemoral prostheses (6) are tested for the transition from the sitting position to the standing position or vice versa and performing human movements such as walking.

The transfemoral prosthesis (6) should generate movements that mimic a human hip while walking and performing sit-ups. This design is limited to two degrees of freedom, i.e., the minimum hip vertical displacement (the CoM center of mass plate (3) motion) and hip rotational movements required to reproduce two-dimensional gait patterns.

Initially, center of mass (CoM) motion was analyzed, and then hip joint angle torque and power data were evaluated while walking at normal speed in order to create conceptual designs for the test platform. Then, a prototype of the test platform system (1) was constructed using two motors, the first motor (11) and the hip unit (5), to enable the center of mass (CoM) motion and hip motion with sufficient torque and power requirements.

In the basic embodiment of the invention, the test platform system (1) includes a vertical guide system (2), a center of mass plate (3) positioned on a rail element (2.1), a transfemoral prosthesis (6), a hip unit (5) that performs the movement of the transfemoral prosthesis (6), a center of mass plate (3) that connects the hip unit (5) and the vertical guide system (2), a connection link (4) that connects the transfemoral prosthesis (6) with the hip unit (5), and a moving belt (12).

In the basic embodiment of the invention, the guide system (2) of the test platform system (1) ensures that upward and downward movement of the center of mass plate (3) (CoM) during the transition of the transfemoral prosthesis (6) from the sitting position to the standing position or vice versa can be simulated. The guide system (2) includes a rail element (2.1), a first motor (11), a ball screw (7), at least one connection plate (13) connecting the ball screw (7) with the vertical guide system (2), and a nut (8). The ball screw (7) converts the rotational movement of the first motor (11) into a linear movement and the nut (8) rotates and moves on said ball screw (7).

In the basic embodiment of the invention, the nut (8) is not secured to the guide system (2) of the center of mass plate (3) (CoM) in the test platform system (1). Therefore, it has a separate degree of freedom. With the present invention, the center of mass (CoM) load of the lower limb device can be carried during the stance phase. By not securing the nut (8) of the ball screw (7) to the center-of-mass plate (3) (CoM), the lower limb device is prevented from generating more torque so as to rotate and move the inertia of the weight of the ball screw (7), the first motor (11), the first motor (11) coupling, and the nut (8), and it is ensured that the lower limb device performs its natural movements.

In the basic embodiment of the invention, the center of mass plate (3) connects the hip unit (5), that performs the rotational movement of the transfemoral prosthesis (6), with a rail element (2.1) in the vertical guide system (2) by way of at least a first connecting element (9). The first motor (11) and the nut (8) are positioned on the ball screw (7). Said ball screw (7) is passed through a screw housing in the center of mass plate (3), which is movably mounted on the rail element (2.1), and is connected to the hip unit (5) by means of at least one connecting element. The center of mass plate (3) is coupled with the nut (8) by means of at least one ball bearing (14), at least one rod (15), and a nut plate (16) which connects the nut (8) to the at least one rod (15). The torque transmitted by the second motor (5) is converted into a linear movement by way of the at least one rod (15). The ball bearing (14) supports the torque-loaded rod (15) and makes it move more smoothly. By converting the torque transmitted by the second motor (5) into the linear movement, the center of mass plate (3) (CoM) moves upward and downward on the rail element (2.1).

The hip unit (5) is a motor unit that simulates hip motions. The transfemoral prosthesis (6) is mounted to the hip unit (5) via a connection link (4). The connection link (4) and the hip unit (5) are connected by means of at least a second connecting element (10). In order for the transfemoral prosthesis (6) to simulate natural hip motion, the hip unit (5) must be able to yield a torque value of 120 Nm and an angular velocity of the hip reaching 40 RPM. In this way, the rotational movement of the hip unit (5) is converted into the linear movement in the vertical guide system (2) in the upward and downward directions, which is carried out smoothly with the help of the rail element (2.1).

In the basic embodiment of the invention, only two basic movements of the hip, namely sitting-standing and walking movements, are simulated in 2 degrees of freedom.

In the basic embodiment of the invention, since the test platform system (1) is a fixed vertical guide system (2), a moving belt (12) is used as the walking surface. Since said moving belt (12) is a separate surface, compatibility with the vertical guide system (2) is checked. Moving belt (12) is a device on which the transfemoral prosthesis (6) simulates natural human movements and cooperates with the guide system (2). Movements on the moving belt (12) can be controlled and speed can be adjusted. The speed of the motor in the moving belt (12) can be controlled.

In other preferred embodiments of the invention, the test platform system (1) can also be used by modifying the relevant prosthesis to incorporate the elements described above for testing the movements of the robotic leg prosthesis, the ankle prosthesis.

A method of operation of the test platform system (1) includes the steps of:

a) connecting a lower limb device to the test platform system (1), b) moving the center of mass (CoM) upwards and downwards during the movement of the guide system (2) along the lower limb device, c) controlling the position of the center of mass (CoM) of a first motor (11) positioned on the vertical ball screw (7) and performing the center of mass (CoM) motion, and at least one nut (8) acting on the ball screw (7) and converting the rotational movement of the first motor (11) into the linear movement, d) controlling the sitting-standing and walking movements of the lower limb device on the moving belt (12) and adjusting the speed.

The limb device tested in an operation method of the test platform system (1) is a transfemoral prosthesis (6).

The operation method of the test platform system (1) also includes the step of performing the rotational movement of the transfemoral prosthesis (6) using a hip unit (5).

The operation method of the test platform system (1) also includes the step of connecting the transfemoral prosthesis (6) with the hip unit (5) by means of a connection link (4).

The operation method of the test platform system (1) also includes the step of connecting the connection link (4) with the hip unit (5) by means of at least a second connecting element (10).

The operation method of the test platform system (1) also includes the step of connecting the hip unit (5) with a vertical rail element (2.1) by means of at least a first connecting element (9).

The operation method of the test platform system (1) also includes the step of increasing the torque value of the hip unit (5) to 120 Nm and the angular velocity thereof to 40 RPM so that the transfemoral prosthesis (6) can simulate natural hip motion.

The limb device tested in an operation method of the test platform system (1) is a robotic leg prosthesis.

The limb device tested in an operation method of the test platform system (1) is an ankle prosthesis.

The invention claimed is:

1. A test platform system for testing lower limb assistive devices, comprising
   a lower limb device,
   a vertical guide system, wherein a movement of the lower limb device is simulated by the vertical guide system during a transition of the lower limb device between positions,
   a second motor, wherein the second motor performs the movement of the lower limb device, and
   a moving belt,
   wherein the vertical guide system comprises:
   a vertical rail element,
   a center of mass plate positioned on the vertical rail element and movable upwards and downwards on the vertical rail element,
   a vertical ball screw connected to the vertical rail element by means of at least one connection plate,
   a first motor, wherein the first motor is positioned on the vertical ball screw and performs a movement of the center of mass plate (CoM),
   at least one nut, wherein the at least one nut acts on the vertical ball screw and converts a rotational movement of the first motor into a linear movement, wherein the center of mass plate is coupled with the nut via at least one ball bearing, at least one rod, and a nut plate, wherein the nut plate connects the nut to the at least one rod element.

2. The test platform system according to claim 1, wherein the vertical ball screw is passed through a screw housing in the center of mass plate and is connected to the second motor.

3. The test platform system according to claim 2, wherein the lower limb device tested is a transfemoral prosthesis.

4. The test platform system according to claim 1, wherein the lower limb device tested is a transfemoral prosthesis.

5. The test platform system according to claim 4, wherein the test platform system is further a hip unit, wherein the hip unit performs a rotational movement of the transfemoral prosthesis.

6. The test platform system according to claim 5, wherein the test platform system further comprises at least one first connecting element, wherein the at least one first connecting element connects the hip unit to the vertical rail element.

7. The test platform system according to claim 6, wherein the test platform system further comprises a connection link connecting the transfemoral prosthesis with the hip unit.

8. The test platform system according to claim 7, wherein a connection between the connection link and the hip unit is realized by means of at least one second connecting element.

9. The test platform system according to claim 1, wherein a torque value of a hip unit reaches 120 Nm and an angular velocity of the hip unit reaches 40 RPM, wherein a transfemoral prosthesis is allowed to simulate a natural hip motion.

10. The test platform system according to claim 1, wherein the lower limb device under test is a robotic leg prosthesis.

11. The test platform system according to claim 1, wherein the lower limb device under test is an ankle prosthesis.

12. A method of an operation of a test platform system, comprising the steps of:
    a) connecting a lower limb device to the test platform system,
    b) moving a center of mass (CoM) upwards and downwards during a movement of a guide system along the lower limb device,
    c) controlling a position of the CoM of a first motor positioned on a vertical ball screw and performing a CoM motion, and at least one nut acting on the vertical ball screw and converting a rotational movement of the first motor into a linear movement,
    d) controlling sitting-standing and walking movements of the lower limb device on a moving belt and adjusting a speed.

13. The method according to claim 12, wherein the lower limb device tested is a transfemoral prosthesis.

14. The method according to claim 13, wherein the method further comprises the step of performing a rotational movement of the transfemoral prosthesis using a hip unit.

15. The method according to claim 14, wherein the method further comprises the step of connecting the transfemoral prosthesis with the hip unit by means of a connection link.

16. The method according to claim 15, wherein the method further comprises the step of connecting the connection link with the hip unit by means of at least one second connecting element.

17. The method according to claim 16, wherein the method further comprises the step of connecting the hip unit with a vertical rail element by means of at least one first connecting element.

18. The method according to claim 12, wherein the method further comprises the step of increasing a torque value of a hip unit to 120 Nm and an angular velocity of the hip unit to 40 RPM, wherein a transfemoral prosthesis is allowed to simulate a natural hip motion.

19. The method according to claim 12, wherein the lower limb device tested is a robotic leg prosthesis.

20. The method according to claim 12, wherein the lower limb device tested is an ankle prosthesis.

* * * * *